United States Patent [19]

Czernilofsky et al.

[11] Patent Number: 5,922,549
[45] Date of Patent: Jul. 13, 1999

[54] PROCESS FOR SCREENING SUBSTANCES HAVING A MODULATING EFFECT ON AN INTERLEUKIN-5 RECEPTOR MEDIATED CELLULAR SIGNAL TRANSMISSION PATHWAY

[75] Inventors: Armin Peter Czernilofsky; Ulrike Weyer, both of Vienna, Austria; Ian G. Young, Hawker, Australia

[73] Assignee: Boehringer Ingelheim International GmbH, Germany

[21] Appl. No.: 08/553,304

[22] PCT Filed: May 27, 1994

[86] PCT No.: PCT/EP94/01735

§ 371 Date: May 29, 1996

§ 102(e) Date: May 29, 1996

[87] PCT Pub. No.: WO94/28170

PCT Pub. Date: Dec. 8, 1994

[30] Foreign Application Priority Data

May 27, 1993 [DE] Germany ............................. 43 17 577

[51] Int. Cl.[6] .................................................. G01N 33/566
[52] U.S. Cl. ........................... 435/7.2; 435/7.1; 435/7.21; 435/7.33; 435/69.1; 435/325; 435/352; 435/363; 435/366; 435/252.3
[58] Field of Search .................................... 435/7.1, 7.21, 435/7.33, 69.1, 325, 352, 363, 366, 252.3

[56] References Cited

U.S. PATENT DOCUMENTS

| | | | |
|---|---|---|---|
| 5,298,429 | 3/1994 | Evens et al. | 436/501 |
| 5,401,629 | 3/1995 | Harpold et al. | 435/6 |
| 5,436,128 | 7/1995 | Harpold et al. | 435/6 |
| 5,453,491 | 9/1995 | Takatsu et al. | 530/350 |
| 5,783,402 | 7/1998 | Konig et al. | 435/721 |

FOREIGN PATENT DOCUMENTS

| | | |
|---|---|---|
| 8928720 | 7/1989 | Australia . |
| WO 92/02639 | 2/1992 | WIPO . |
| WO 92/13063 | 8/1992 | WIPO . |

OTHER PUBLICATIONS

Himmler, A., et al., "Functional Testing of Human Dopamine $D_1$ and $D_5$ Receptors Expressed in Stable cAMP–Responsive Luciferase Reporter Cell Lines," *J. Receptor Res.* 13(1–4):79–94 (Feb. 1993).

Lamb, N.J.C., et al., "Demonstration in Living Cells of an Intragenic Negative Regulatory Element within the Rodent c–fos Gene," *Cell* 61:485–496 (1990).

Schoönthal, A., et al., "Requirement for fos Gene Expression in the Transcriptional Activation of Collagenase by Other Oncogenes and Phorbol Esters," *Cell* 54:325–334 (1988).

Chihara et al, *JPN. J. Thorac. Dis.* 1993, 31(suppl.) pp. 165–171.

Godall et al, *Growth Factors* 1993 V. 8, N. 2, pp. 87–97.

Banks et al, *Analytical Biochem* 230, 1995, pp. 321–328.

Voraberger, G., et al., "Cloning of the Human Gene for Intercellular Adhesion Molecule 1 and Analysis of its 5'–Regulatory Region," *J. Immunol.* 147(8):2777–2786 (1991).

Sakamaki et al, *EMBO J* 10(10) 1992, pp.3541–3549.

Cosman *Cytokine* 5(2) 1993, pp. 95–106.

Miyajima et al, *Annu. Rev. Immunol* 1992, pp.295–331, vol. 10.

Lee et al, J. Immunol. 151, 1993, pp. 6135–6142.

Takashi et al, *J. Cell Biochem* Suppl 17A, Jan. 1993, p. 77.

Chiba et al, *Nature* 362, 1993, p. 641.

Stahl et al, *Cell* 74, 1993, pp. 587–670.

Lee et al Blood 84(10 Suppl 1) 1994, p. 15a.

Jato et al *EMBO* 12(11) 1993, pp. 4181–4189.

*Primary Examiner*—Garnette D. Draper
*Attorney, Agent, or Firm*—Sterne, Kessler, Goldstein & Fox P.L.L.C.

[57] ABSTRACT

A process is disclosed for screening substances having a modulating effect on the interleukine-5-receptor-dependent signal tranmission path in mammal cells. Test substances are applied on cells which express the functional interleukine-5-receptor and are transformed with a recombinant DNA containing a reporter gene and a regulatory sequence functionally linked thereto which is sensitive to a change in concentration of a secondary messenger substance of the interleukine-5-receptor-dependent signal transmission path. Substances specific to the interleukine-5-receptor-dependent signal transmission path and with potential pharmacological effect may be identified by this process.

26 Claims, 6 Drawing Sheets

PROCESS FOR SCREENING SUBSTANCES HAVING A MODULATING EFFECT ON AN INTERLEUKIN-5 RECEPTOR MEDIATED CELLULAR SIGNAL TRANSMISSION PATHWAY

The present invention relates to a process for finding pharmacologically active substances by measuring the modulating effect of substances on an interleukin-5 receptor mediated signal transmission pathway in human or animal cells.

Conventional so-called "radioligand tests", in which a substance is investigated as to what extent it can displace a ligand bound to a receptor, which are used for finding pharmacologically active substances, can only be used to identify substances which affect the binding of known ligand receptor binding sites. These tests cannot tell whether the binding substance has an agonistic or antagonistic activity.

Transmembrane signal transmission systems of higher eukaryotic cells frequently consist of the following membrane-bound components:

a) a cell surface receptor which may optionally consist of a plurality of subunits; optionally b) a guanine-nucleotide binding and GTP cleaving regulatory protein, which is referred to as a G-protein and may be coupled both to the receptor and to its effector;

c) so-called "effectors", which often lead to a change in concentration of secondary messenger molecules, such as cAMP, DAG, $IP_3$, etc., e.g. an ion channel or adenylate cyclases, guanylate cyclases or phospholipases; and/or d) various kinases.

Cell surface receptors recognise the appropriate ligands from a plurality of extracellular stimuli. The binding of the ligand to the receptor activates a signal cascade. In the case of G protein coupled receptors, the signal transmission pathway of which is relatively well understood and which mediate the activities of very different extracellular signals, this begins with the activation of the heterotrimeric G-protein.

Lower molecular weight secondary messengers such as cAMP (cyclic AMP), triggered by activation of the adenylate cyclase, cGMP (cyclic GMP), triggered by activation of the guanylate cyclase, or inositol-1,4,5-triphosphate ($IP_3$) and diacylglycerine (DAG), triggered by activation of phospholipases, such as phospholipase C or, when hydrolases are involved, phospholipase D (Billah et al., 1989), in turn bring about intracellular changes, including the selective phosphorylation of proteins by activation of protein kinases (e.g. PKC by $IP_3$/DAG, PKA by cAMP), influencing the regulation of the transcription of certain genes and proliferation. (An antagonistically active substance may wholly or partially cancel the interaction caused by an agonistically active substance and the consequent change in concentration of the second messenger, or may itself lead to a reverse functional effect.) Using this signal transmission system, cells can communicate with one another and coordinate their development or the activities which they trigger.

Since a single receptor subtype (possibly in the same cell or in different cells) may be coupled to more than one effector and numerous receptor subtypes may activate the same effectors, complicated signal transmission networks are formed. The transcription factors which are activated as a result of the activation of the receptor in the signal transmission cascade (such as CREB-protein, AP1-protein) interact with regulatory DNA elements. Examples of this are CRE (CRE-element, "cAMP responsive element") or TRE (TRE="TPA responsive element"; TPA=phorbol-12-myristate-13-acetate=phorbolester), which bind CREB or AP1: many genes whose transcription is regulated by cAMP (e.g. rat somatostatin, human-a-gonadotropin, c-Fos), contain a conserved sequence, in the 5'-flanking region, as a regulatory element. The CRE-sequence is identical or similar to the palindromic octamer TGACGTCA (Montminy et al., 1990). TRE-elements contain the very similar heptameric motif TGAGTCA, which differs from the CRE-element consensus sequence only in a single nucleotide (Deutsch et al., 1988). The TRE-motif, or very similar motifs, have been identified in numerous genes the transcription of which is activated by phorbolesters (Angel et al., 1987a and b; Lee et al., 1987). Surrounding DNA sequences or protein-protein interactions with other factors determine, inter alia, the concrete regulatory phenomena at a specific gene.

Other regulatory DNA-elements are the so-called "SRE-elements" which respond to serum factors ("serum responsive element"; Treisman, 1985). SRE-elements are inducible cis-elements which consist of 20 base pairs with a dyadic symmetrical structure. SRE-elements respond to various growth factors; it was recently reported that SRE is the crucial target for c-fos induction by various cytokines (Hatakeyama et al., 1989). The motifs which respond to the change in concentration of glucocorticoids are referred to as "GRE-elements" (Yamamoto, 1985; Scheidereit et al., 1986; Jantzen et al., 1987; Strähle et al., 1987).

As a result of the complexity of the network of the signal transmission pathways, there may be so-called "crosstalk" between signal transmission pathways, e.g. the adenylate cyclase and phospholipase C signal transmission pathway. The term "crosstalk" refers to the phenomenon in which the influencing of one effector system leads to influencing of another (Sassone-Corsi et al., 1990; Houslay, 1991). The phenomenon of crosstalk is used physiologically for the integration or linking of signals in order to produce a redundancy of signals or ensure communication of the various signal transmission pathways. Crosstalk may occur at various levels of the signal transmission pathway. One possible cause of pathological changes to the cell is disruption of these interactions, e.g. when a certain receptor no longer interacts correctly in the physiological sense with an effector system.

Receptors which are not coupled to G-proteins include the cytokine receptors. These are assumed to be coupled to numerous signal transduction pathways which in turn overlap for different receptors, so that there is multiple crosstalk within the cell.

Cytokines play an important part in the coordination of immune and inflammatory reactions (lymphokines and monokines), in fighting off viral infections (interferons) and in haematopoesis ("colony stimulating factors", CSF). They regulate the proliferation, differentiation and function of a number of cells within haematopoetic, lymphoidal or other organ systems. Each individual cytokine exerts its effect on various cell types, and individual cells often react with a plurality of cytokines, so that cytokine-producing cells and cells which are regulated by cytokines form a complex intercellular network in which the cytokines act synergistically or in opposition. The spectrum of the biological activity of a cytokine is determined, inter alia, by the number of different cell types which express specific receptors for the cytokine.

Interleukin-3 (IL-3) and granulocyte-macrophage-colony-stimulating-factor (GM-CSF) are examples of pleiotropic factors which stimulate multipotent haematopoetic cells and precursor cells for a whole range of haematopoetic lines. Interleukin-5 (IL-5) on the other hand has a much narrower range of activity and acts predominantly on eosinophilic precursor cells (Miyajima et al., 1992).

Analysis of their protein structures has shown that all cytokine receptors are membrane-bound glycoproteins which consist of an extracellular N-terminal domain, a single transmembrane domain and a cytoplasmic domain. The extracellular domains have a number of common structural components according to which the cytokine receptors can be ascribed to numerous receptor gene families the members of which presumably originate from the same precursor genes (Gillis, 1991). The IL-5-receptor gene belongs to the haematopoetin-receptor gene family. The members of this family contain characteristic conserved cysteine groups which occur individually or in multiple copies in the extracellular domain. They also contain a tryptophan-serine-X-tryptophan-serine motif (where X may be any amino acid), which is frequently located in the extracellular domain close to the transmembrane domain. Finally, receptors of this family have individual or multiple copies of the fibronectin type 3 binding motif, scattered over the entire extracellular domain (Gillis, 1991).

Apart from the IL-5-receptor (both subunits), both subunits of the receptors for IL-3, IL-6 and GM-CSF, IL-4, IL-7, erythropoetin (EPO) and "leukaemia inhibitory factor" (LIF)-receptors, the β-subunit of the IL-2 receptor and the receptors for growth hormone (GH), prolactin and G-CSF also belong to the haematopoetin receptor family.

The IL-5-receptor consists of an a-subunit which contains the specific cytokine binding domain, and a β-subunit which contributes to the formation of a high affinity of the receptor for IL-5 and is necessary for signal transduction. The DNAs coding for the human (Tavernier et al., 1991) and the murine (Takaki et al., 1990) α-subunit, and the human (Tavernier et al., 1991) and murine (Devos et al., 1991; Takaki et al., 1991) β-subunit of the IL-5 receptor were cloned. The receptors for IL-5, IL-3 and GM-CSF have an identical β-subunit (Kitamura et al., 1991; Tavernier et al., 1991). If more than one of the three receptors is expressed on a cell, there may therefore be "cross-talk" between the cytokines at the receptor level.

The subunits of the cytokine receptors, unlike receptors for growth factors such as EGF or PDGF, do not contain any intrinsic tyrosine kinase activity. However, it has been shown that stimulation of the IL-5, IL-3 and GM-CSF receptor by the ligand in question induces rapid tyrosine phosphorylation of certain cellular proteins (Koyasu et al., 1987; Isfort et al., 1988; Morla et al., 1988; Murata et al., 1990). A tyrosine kinase has been identified which after stimulation with GM-CSF associates with the β-subunit of the receptor (Hanazono et al., 1993). Other processes which occur during GM-CSF-induced signal transmission are the activation of $p21^{ras}$ (Satoh et al., 1991, 1992) and c-raf (Carroll et al., 1990), whereas for the IL-3-induced signal transduction, besides activation of $p21^{ras}$ (Satoh et al., 1991, 1992) and c-raf (Carroll et al., 1990), activation of protein kinase C (Whetton et al., 1988) and phosphorylation of "mitogen-activated protein" (MAP)-kinases (Welham and Schrader, 1992) has also been demonstrated. However, up till now, the precise sequence of these processes within the entire signal transduction cascades has not been determined.

The genes which are induced after stimulation of cytokine-receptors via components of the signal transduction machinery have largely not yet been identified. Thus, little is known of the regulatory elements in the promoters of such genes. For example, stimulation of IL-6 receptors leads to the activation of a specific DNA-binding protein, NF-IL-6, which brings about expression of the genes by binding to IL-6 responsive elements in the promoter area of the target genes and thereby brings about IL-6-dependent biological effects (Akira et al., 1990). The c-fos proto-oncogene, which contains multiple inducible sequence elements in the promoter region (Verma and Sassone-Corsi, 1987) is induced by IL-2, IL-3 and EPO, whilst the "serum-response-element" (SRE) present in the c-fos promoter is involved in its induction, inter alia (Hatakeyama et al., 1989, 1992).

The IL-5 receptor is activated by binding of its ligand interleukin-5 (IL-5). IL-5 is a peptide hormone which is produced by T-cells and mast cells and has an essential function in end differentiation of the eosinophiles.

Almost nothing is known about the signal transmission pathways which are coupled to the IL-5 receptor. Apart from the phosphorylation of some as yet unidentified cellular proteins (Murata et al., 1990) no processes in the signal transduction triggered by stimulation of the IL-5 receptor have been explained. Since the three cytokines IL-5, IL-3 and GM-CSF have different biological functions, it is possible that apart from the β-subunit which is common to all three receptors, the cytokine-specific α-subunits of the receptors also play a part in the induction of intracellular signal pathways, particularly cytokine-specific signal transmissions and functions (Tominaga et al., 1992).

Therefore, no clear conclusions as to the signal pathways coupled to the IL-5 receptor can be drawn from the knowledge of the signal transmission processes triggered by IL-3 receptor or GM-CSF receptor activation. Since no genes have yet been identified which are induced after stimulation of the IL-5 receptor, nothing is known, either, of regulatory elements present in the promoter region of such genes, responding to signal transmission pathways which are set in motion by activation of the IL-5 receptor.

The activation of the IL-5 receptor by binding of its ligand has been connected with various diseases which are accompanied by eosinophilia, i.e. an increase in the eosinophiles in the blood. These include autoimmune diseases, transplant rejections, allergic diseases, certain parasitic diseases and asthmatic diseases. Approaches which have hitherto been proposed for causal therapy of such diseases consist on the one hand in the administration of the soluble α-subunit of the IL-5-receptor as an antagonist (EP-A 0 492 214) and, on the other hand, starting from the crystalline structure of IL-5, in a rational design of antagonist or agonists (Milburn et al., 1993).

Recently, screening methods have been developed which make it possible to find drugs for treating pathological conditions which are specific to a certain receptor or receptor subtype and which also specifically influence the receptor mediated signal transmission pathway. These methods are based on the principle that the modulating effect of substances on the receptor mediated signal transmission pathway can be detected by means of the expression of genes:

An assay system described by King et al., 1990 is based on influencing the signal transmission pathway which is used by the G protein coupled pheromone receptors of *Saccharomyces cerevisiae* in which, in the yeast cell, the reaction to binding of an agonistically active compound to a receptor transfected into the yeast cell is measured by colorimetry.

Montmayeur and Borelli, 1991, described an assay which is based on influencing the adenylate-cyclase signal transmission pathway by activating G protein coupled receptors ($D_2$-receptors and the β-adrenergic receptor were used).

Himmler et al., 1993, developed a functional test in which the activity of the receptor coupling (human dopamine D1- and D5-receptor) to the cAMP-signal transmission pathway was measured by the transcriptional activation of a reporter gene.

The assays known hitherto are limited to measuring the expression of genes which is regulated by the concentration of cAMP, a messenger substance of one of the signal transmission pathways of G protein coupled receptors.

By contrast, the aim of the present invention was to provide a screening method with which substances could be identified which modulate an IL-5 receptor mediated signal transmission pathway, the mechanisms and messenger substances of which are very little understood. In particular, the present invention was to provide a process which is automatable and thus suitable for screening substances at high throughput rates and which also makes it possible to investigate complex mixtures of substances such as extracts from organisms, for their content of pharmacologically active substances.

The identification of substances on the basis of their ability to modulate an IL-5 receptor mediated signal transmission pathway, particularly agonists of the IL-5 receptor, forms the starting point for the development of drugs which are used for the treatment of diseases involving the modulation, and frequently the activation, of the IL-5 receptor.

Within the scope of the present invention it has been shown that, in cells which express the structural elements required for functioning of the IL-5 receptor and the components of the IL-5 receptor mediated signal transmission pathway (such cells are hereinafter referred to, for simplicity's sake, as "cells which express the functional IL-5 receptor") and which are transformed with a reporter gene construct containing regulatory DNA elements, the reporter gene construct is induced by activation of the IL-5 receptor after binding of its ligand.

In view of the limited knowledge of the IL-5 receptor mediated signal transmission pathway these results were surprising, particularly as it was impossible to predict whether, or which of the regulatory DNA elements characterised hitherto, would respond to a messenger substance of the signal transmission pathway set in motion by the IL-5 receptor.

The present invention relates to a process for determining the modulating effect of a substance on a receptor mediated signal transmission pathway in the human or animal cell. The process is characterised in that the modulating effect of the substance on a component in the signal transmission pathway initiated by activation of the IL-5 receptor is determined by incubating mammalian cells which are a) transformed with a recombinant DNA, containing a reporter gene and a regulatory sequence which responds to a change in concentration of one or more secondary messenger substances of the signal transmission pathway coupled to the IL-5 receptor, so that the expression of the reporter gene is modulated by a change in concentration of the messenger substance, and which further b) express the functional interleukin-5 receptor, with the test substance, measuring the concentration of the reporter gene product and investigating whether the activity of the test substance found is selective for the IL-5 receptor mediated signal transmission pathway.

The definition "interleukin-5 receptor mediated signal transmission pathway" within the scope of the present invention also includes an interleukin-5 receptor mediated signal transmission mechanism which optionally consists of more than one signal transmission pathway.

The definition "component in the signal transmission pathway" includes all mechanisms of the molecules involved in the signal transmission pathway including the IL-5 receptor itself or its subunits.

If one is looking for inhibitors of the IL-5 dependent signal transmission pathway, the test substances are investigated for their antagonistic effect, by placing them on the cells together with IL-5, the IL-5 generally being added to the cells simultaneously with or after the test substance.

The recombinant DNA which responds to changes in the secondary messenger substances and is also part of the present invention is hereinafter referred to as "sensor-DNA". A reporter gene is defined by the fact that its expression product is detectable and quantifiable by a measurement of a signal proportional to its concentration.

Cells which are transformed with sensor DNA and express the IL-5 receptor are hereinafter referred to as "test cells"; these cells are also a subject matter of the present invention.

The term "IL-5 receptor" according to the present invention denotes the functional IL-5 receptor, whilst this definition will also include any IL-5 receptor subtypes present. By "functional receptor" is meant, according to the present invention, on the one hand the natural IL-5 receptor consisting of the $\alpha$- and $\beta$-subunits of the same species, and also in the test cells, particularly human cells, viable combinations of $\alpha$- and $\beta$-subunits of the IL-5 receptor of different species, e.g. the $\alpha$-subunit of the human receptor and the $\alpha$-subunit of the murine receptor, or vice versa. A functional receptor according to this definition is also present if, in a cell in which a $\beta$-subunit naturally interacts with the $\alpha$-subunit of another receptor, e.g. the IL-3- or GM-CSF receptor, the $\alpha$-subunit of the IL-5 receptor is introduced into the cell and expressed therein, whilst in this case the $\alpha$-subunit may also come from a different species, provided that functional cooperation of the two subunits is ensured with respect to initiation of the signal transduction pathway.

The recombinant DNA which contains one or more sequences coding for the subunit or subunits of the IL-5 receptor is hereinafter referred to as "receptor-DNA".

Suitable starting cells for preparing test cells are cells which already endogenously contain the complete functional IL-5 receptor, but also cells which contain the components of the receptor-coupled signal transduction pathways which are required for induction of the sensor-DNA. For such cells to be suitable it is not essential that they express the entire IL-5 receptor or even only one of its subunits beforehand. If one or both subunits is absent the cell may be transformed, not only with the sensor-DNA, but additionally with the sequence coding for the missing receptor subunit or subunits.

In one embodiment of the invention the test cell is derived from a cell which naturally expresses both subunits required for the functional IL-5 receptor.

According to another embodiment of the present invention, the test cell is derived from a starting cell which expresses only the $\beta$-subunit; in this case the cell is transformed not only with sensor DNA but with a plasmid which contains a DNA sequence coding for the $\alpha$-subunit of the IL-5 receptor.

In another embodiment of the invention, the starting cell for the test cell does not naturally contain either the $\alpha$- or the $\beta$-subunit of the IL-5 receptor. In this case, the cell has to be transformed with both DNA sequences, which may occur together on one plasmid or on separate plasmids.

When substances are to be investigated in terms of their pharmacological activity for the treatment of pathological conditions in humans, the receptor-DNA preferably contains the sequence coding for the human IL-5 receptor. (The process according to the invention is preferably used for finding substances which are suitable for treating pathological conditions in humans. It may, however, also be used for screening substances which are used for treating animals; in this case the corresponding animal IL-5 receptor is used.)

Preferably, cells for preparing the test cells are selected on the basis that after stimulation with substances which increase the concentration of secondary messenger substances, as a function of the IL-5 receptor, exhibit a strong expression of the reporter gene. This is conveniently tested by transiently transforming cells which express a functional IL-5 receptor using sensor DNA and investigating the concentration of the reporter product after stimulation of the receptor with IL-5.

The starting cells for the test cells may be, in particular, cells which are known to express the IL-5 receptor or a receptor which contains the β-subunit, or cells which can be assumed, on the basis of their origin or function in the organism, to express one of the receptors in question, particularly haematopoietic precursor cells. Expression of the receptor may optionally be confirmed by binding assays and/or proliferation assays in which the growth of the cells in the presence of the ligands in question (IL-5, IL-3 or GM-CSF) is determined.

Examples of suitable starting cells are factor-dependent cell lines established from bone marrow cells; the production of such cell lines which express the β-subunit has been described for example by Dexter et al., 1980, for murine cells. Within the scope of the present invention, an example of such a murine cell line was transfected with the α-subunit of the murine IL-5 receptor and used as a test cell. Another example of suitable test cells consists of IL-5 dependent haematopoietic cells, e.g. cells of the cell line TF-1 described by Kitamura et al., 1989 and 1991.

In cells in which both subunits are of murine origin, e.g. the murine cell line 1H3, the α- and possibly the β-subunit as well may be switched off, e.g. by homologous recombination, and replaced by the corresponding human sequence.

In principle, mammalian cells from any species may be used as starting cells, but human cells are preferably used. If non-human cells are used, it is preferable to use cells which are transformed with human IL-5 receptor DNA (β- and/or α-subunit).

Another precondition for suitability of a cell as a test cell, for the purposes of the present invention, is its stability. In order to test the stability of the cells (viability, stable integration of the foreign DNA into the genome), tests are carried out with the test cells under identical conditions over long periods of time and the reproducibility of the measurements is checked.

The sensor-DNA is preferably located on a plasmid which can be replicated in high copy numbers in a suitable host organism, preferably E. Coli, and after transfection into mammalian cells and integration into the host genome, enables expression of a reporter gene to take place under the control of regulatory elements. This is preferably a shuttle vector which contains an expression cassette for the reporter gene (sensor-DNA) and a selectable marker for mammalian cells as well as at least one replication origin and a marker for the replication and selection in E. coli.

In order to produce permanent cell lines which contain the sensor DNA stably integrated in their genome, the vector contains a dominant selection marker. The use of a specific selection marker is not critical; suitable ones include, for example, the gene for neomycin phosphotransferase (neo) which imparts resistance to the antibiotic geneticin (G-418) (Southern and Berg, 1982), the DHFR-gene (dihydrofolate reductase) for DHFR-deficient cells, the gene for xanthine-guanine-phosphoribosyltransferase (gpt), which imparts resistance to mucophenolic acid (Mulligan and Berg, 1981) or the hygromycin-B-phosphotransferase gene (hph; Gritz and Davies, 1983). Examples of promoters which drive the selection marker gene are the SV40-Early-promoter, the cytomegalovirus promoter (CMV-promoter), the promoter of the thymidine kinase gene of the Herpes simplex virus (TK-promoter), the Rous Sarcoma virus (RSV) long terminal repeat (LTR). The plasmids are preferably designed so that individual important elements such as the reporter gene, the promoter for the reporter gene, the regulatory sequences for the selection marker, can easily be replaced or changed, in order to adapt to any modified requirements resulting from the special application, e.g. as a result of the use of a different cell line. Such measures consist, for example, of incorporating multicloning sites in front of the promoter or promoters or in front of the reporter gene, in order to permit the cloning of regulatory sequences which modulate the promoter or various reporter genes.

When selecting a suitable reporter gene the starting premise was to provide an automatable, preferably non-radioactive, assay with high sensitivity.

Within the scope of the present invention, theoretically any reporter genes which satisfy these preconditions may be used:

Alkaline phosphatase may be measured with a high degree of sensitivity when a chemiluminescent substrate is used, but it does have the disadvantage that numerous mammalian cells express this enzyme relatively strongly. Therefore, it can generally only be considered as a reporter gene for those cell lines which do not express it or express it only slightly.

The expression products of the β-galactosidase- and β-glucuronidase-gene can cleave the corresponding methylumbeliferyl-galactoside or -glucuronide to form fluorescent groups. These enzyme reactions are monitored using established fluorescence assays (Wieland et al., 1985; Kricka, 1988).

The expression of chloramphenicol-acetyltransferase (CAT) can be detected with relatively great sensitivity but the assay does have the disadvantage that it is radioactive and difficult to automate (Hartmann, 1991).

Preferably, within the scope of the present invention, the gene which codes for *Photinus pyralis* luciferase (De Wet et al., 1987) is used as the reporter gene. This enzyme has the advantages that with its substrate luciferin and the addition of ATP it produces high yields of bioluminescence which can be measured by established, automated methods, and that this enzyme is not produced endogenously by mammalian cells. In addition, luciferase has a relatively short in vivo half life and is not toxic even at high concentrations (Hartmann, 1991; Brasier et al., 1989).

In the construction of sensor DNA the reporter gene is placed under the control of promoters which contain modulatable regulating elements such as TRE- and/or CRE- and/or SRE- and/or GRE-elements. Since the signal transduction pathways of the IL-5 receptor are not specifically known in detail, the most suitable sensor-DNA constructions are determined empirically in preliminary trials. To do this, a cell which expresses a functional IL-5 receptor is transiently transformed with various sensor DNA constructs, on the one hand changing the reporter gene and on the other hand changing the control sequences, and the measurement of the reporter gene product is tested for its sensitivity by measuring the concentration of the reporter gene product after stimulation of the receptor with an agonist, preferably IL-5. Suitable regulatory sequences in the sensor DNA are all the DNA elements which bring about activation of the promoter, e.g. elements selected from the group comprising TRE, CRE, GRE or SRE or those which contain a combination of these various elements. With a sensor DNA of this kind containing two or more different elements, activation of numerous signal transduction pathways individually or parallel activation of numerous signal transduction pathways is covered. The choice of sensor DNA for the test cell development is made on the basis of achieving maximum possible inducibility of the reporter gene in the given cell system. The regulatory DNA region may be a naturally occurring promoter region but it may also be produced artificially.

The complete promoter of a gene which is inducible by a plurality of secondary messenger substances may optionally be used, e.g. the 5'-regulatory sequence of the ICAM-1-gene (intercellular adhesion molecules 1) or the c-fos gene. A natural promoter responding to activation of the IL-5 receptor and containing multiple regulatory elements, e.g. the ICAM-1-promoter which contains, inter alia, TRE-, NKKB-, SP1- and AP2-elements (Voraberger et al.,) or the c-fos-promoter which contains, in addition to CRE- and SRE-elements inter alia, regulatory sequences designated the "SIF-E-element" and the "$AP_1$-like element" (Hipskind and Nordheim, 1991) may be investigated as to which of its elements is responsible for the activation. This may involve investigating artificial promoter sequences, which have various mutations and/or deletions compared with the natural promoter, for their activatability. Starting from the results of such tests, the promoter may be further optimised, if desired, for example by using multiple copies of the element or elements identified as being crucial.

If desired, known natural or synthetic promoters are modified by shortening them to the minimum sequence required for the promoter function. When constructing a sensor-DNA in which the reporter gene is driven by a non-natural promoter, one or more elements, e.g. TRE- and/or CRE- and/or SRE- and/or GRE-regulating elements which modulate the promoter are preferably placed before the weak promoter elements. Anyone skilled in the art is familiar with the control sequences which are suitable for expression in specific mammalian cells; the choice can be made first of all on the basis of the relevant literature (e.g. Landschulz et al., 1988, Turner and Tjian, 1989) and narrowing down or optimisation may be carried out using the above-mentioned transient transfection experiments which are easy to carry out. Examples of suitable promoters are the β-globin promoter and the TK promoter.

When selecting the regulatory sequence (including its flanking sequences) contained in the sensor DNA, the elements known from the literature are taken as starting substances (e.g. for TRE- or CRE-elements cf. Montminy et al., 1990; Deutsch et al., 1988) and these are tested in preliminary tests for their suitability with respect to the sensitive detection of the inducibility of the reporter gene in a given cell system. Examples of suitable TRE-elements, including their flanking sequences, are the sequences of somatostatin, "vasoactive intestinal peptide", cytomegalovirus enhancer, bovine leukaemia virus long terminal repeat (BLV LTR) (CRE-elements) and ICAM-1, collagenase and parathyroid hormone (TRE-elements). If the motifs contained in the natural sequences do not have a perfect consensus sequence, they, and possibly their adjacent sequences, may be changed by replacement of one or more nucleotides, if a perfect consensus sequence is necessary or desirable.

The regulatory elements and the sequences flanking them may be produced synthetically or they may be of natural origin.

In order to intensify the modulating effect of a secondary messenger substance on the reporter gene expression, a construct may optionally be used containing a plurality of homologous or heterologous regulatory sequences in tandem. When arranging the individual elements of the construct, the spacing of the elements from one another is selected so as to ensure the binding of the transcription factor to the elements. The optimal spacing of the regulatory elements from one another, the measurement of which involves considerations regarding the steric arrangement, is determined emperically in preliminary trials, and optionally so is the spacing from other regulatory DNA-elements which affect the transcription, e.g. the TATA box. In multiple regulating sequences the elements and/or the flanking sequences may be identical or at least partly different, the latter being preferred for the tandem construction.

As sequences flanking the regulatory element, which have been found to affect the regulating properties of the elements, it is preferable to use, particularly in the immediate vicinity thereof, the sequences which naturally surround the special regulatory element (Montminy et al., 1990; Deutsch et al., 1988). The sequence or its arrangement is determined empirically.

The elements of the sensor DNA and the marker gene used for selection may possibly be situated on two separate plasmids, one containing the reporter gene construct (including the expression control sequence which contains the regulatory sequence) and one containing the selection marker gene construct. (Examples of suitable selection marker gene constructs are the plasmids pRSVneo, pSV2neo, pRSVgpt, pSV2pt, the construction of which can be found in the relevant textbooks, e.g. "Cloning Vectors".) When separate plasmids are used the cells are co-transfected with both plasmids and selected for the marker. The presence of the selection marker leads one to conclude that the cell also contains the reporter gene construct, as it is known that co-transformation of two genes which are located on DNA-segments not physically connected to one another frequently leads to the expression of both co-transformed genes (Winnacker, 1985).

With regard to the measuring arrangement to be used in the test procedure it is advisable to optimise the ratio between maximum change and the normal value of the measuring signal, preferably by changing the construction of the sensor DNA, e.g. by structural change of the promoter arrangement. The background signal is preferably low enough to detect induction of the reporter gene expression with a high degree of sensitivity, but high enough to be able to determine the limits of detection with regard to the negative control. The receptor DNA construct is subject to fundamentally the same considerations as the sensor DNA construct, except that the receptor sequence or sequences are preferably placed under the control of a strong structural promoter. The receptor DNA can be obtained by conventional methods of molecular biology, e.g. by preparing the cDNA starting from an RNA preparation from cells which express the IL-5 receptor, using reverse transcriptase PCR, the primers being constructed on the basis of the published sequence or sequences, and cloning it into a suitable vector. The cDNA may also be amplified out of a cDNA library using PCR.

In the case of the receptor DNA, the sequence coding for the receptor subunit and the dominant selection marker may also be found on separate plasmids with which the cells are co-transformed.

Transfection of the cells with sensor or receptor DNA is carried out using conventional transfection methods (cf. for example Potter et al., 1984; Felgner et al., 1987), preferably using the electroporation, calcium phosphate precipitation or the lipofection method.

In order to test the selectivity of a test substance for the IL-5 receptor, test cells for various other receptors are prepared, for further control tests, and treated with the substance. If a substance should only specifically influence the IL-5 receptor, as is generally the case with regard to the specificity of a drug, the substance should modulate only this one receptor.

In the control cells, the control receptor may, in principle, either occur endogenously or be transformed into the cell. If the sensor DNA used for the IL-5 receptor test cell is also measurably induced by the stimulation of this receptor by an agonist, e.g. IL-5, the IL-5 receptor test cell is suitable as the control cell if the sequence coding for the control receptor is endogenously present or has additionally been transformed into the cell. (The term control receptors also includes those receptors which have the β-subunit in common with the IL-5 receptor, e.g. the IL-3 receptor.) Also in this case it is possible to use as the control cells those cells which contain this sensor DNA and the control receptor but not the IL-5 receptor. If, on the other hand, the sensor DNA used for the IL-5 receptor test cell is not induced by stimulation of the control receptor, a suitable sensor DNA must be determined emperically, starting from the elements known from the literature (see for example Montminy et al., 1990; Deutsch et al., 1988) which are investigated in preliminary tests for their suitability with respect to the sensitive detection of the inducibility of the reporter gene in the given cell system. The sensor DNA is then transformed into the cell, together with the coding sequence for the control receptor, if the latter is not endogenously present.

The selectivity of the modulating effect of the substance on the interleukin-5 receptor mediated signal transmission pathway is preferably tested by applying it under identical conditions to control cells which express a control receptor and which are transformed with a sensor DNA, the regulatory sequence of which responds not only to the interleukin-5 receptor but also to the activation of the control receptor, and comparing the concentration of the reporter gene product in the cells which express the interleukin-5 receptor with that in the control cells.

After transformation of the cells with receptor-DNA the positive clones are investigated for the level of expression of the receptor, e.g. using binding assays in which known radiolabelled agonists and antagonists are used.

The number of receptors can be determined in molecules per cell using Scatchard blots (Human Pharmacology, 1991).

Preferably, a clone with a receptor number corresponding as far as possible to the physiological receptor concentration is selected from the stable transformants which contain receptor DNA. (If the receptor number is too high, incomplete and possibly non-specific coupling may occur or, in addition to specific coupling, non-specific coupling may occur, thereby possibly activating other effector systems. If the receptor number is too low the signal may be too low to be picked up by the measurement.)

By "modulating" effect is meant an agonistic or antagonistic effect on an IL-5 receptor mediated signal transmission pathway.

Substances which have shown an inhibitory effect on the IL-5 receptor mediated expression of reporter genes in the test procedure can be tested in a subsequent step to see whether they inhibit the IL-5 dependent proliferation of cells. In a process of this kind the inhibiting effect of the substance on the proliferation of the cells is determined by taking cells which express the functional IL-5 receptor in addition to receptors for other growth factors and are dependent in their growth on the presence of IL-5 of at least the ligand for one of these receptors, e.g. IL-5, incubating these cells with IL-5 on its own and in a subsequent mixture with IL-5 and the test substance and measuring the proliferation of the two mixtures.

There is a wide variety of methods for such proliferation assays; they may, for example, be carried out in 96-well microtitre plates and can easily be automated. Examples of such assays are those based on the measurement of $[^3H]$-thymidine or bromodeoxy-uridine(BrdUrd) incorporation (measurement of the incorporation of BrdUrd, for example, by means of the binding of fluorescence-labelled anti-BrdUrd-antibodies). Another type of proliferation assay is based on the measurement of dyes formed by the reaction of suitable substrates using cell enzymes. One of the methods developed on this principle is the commercially obtainable tetrazolium salt method (MTT method) in which the concentration of the dye formazane formed by reaction of a tetrazolium salt by means of dehydrogenase is measured spectrophotometrically.

Examples of cells which are suitable in the proliferation assay are the IL-5 dependent haematopoetic cells, e.g. cells of the cell line TF-1 described by Kitamura et al., 1989 and 1991.

The substances which are to be tested for their potential pharmacological activity using the process according to the invention may be natural or synthetic substances, and either pure substances or mixtures of substances (e.g. plant extracts, fermentation liquors, etc.) may be used. Among the pure substances, low molecular weight synthetic organic compounds are of particular interest. The substances which are to be picked up by screening include mainly substances which bind to the ligand binding site of the receptor, allosterically active substances and substances which act non-competitively with regard to the ligand binding site. These substances may be of a peptidic or non-peptidic nature.

Preferably, the substances are applied to the cells in serial dilutions in order to obtain the widest possible range of concentrations. The incubation time is emperically determined, e.g. by treating the given test cells with known receptor agonists and measuring the time from which the induction of the reporter gene expression can be reproducibly measured. The incubation time is generally set to this time and is generally at least 1 hour. The number of cells depends primarily on the detection limits of the measuring signal and the growth stage which the cells have reached, whilst the lower limit is further defined by the technological ability to distribute the cells uniformly over the test units. When microtitre plates with 96 wells are used the number of cells will be, for example, about 1000 to 100,000 cells per test unit, but the number may be lower if the measuring signal is suitably sensitive and the cells are precisely distributable. The growth stage at which the cells are used depends on the cell type specific properties of the starting cell and is, moreover, determined primarily by the receptor in question (in different receptors, the same effector system can be activated differently or to different intensities depending on the growth stage); the growth stage and number of cells are thus also determined emperically in preliminary trials by determining the kinetics of the reporter gene expression in pretest and test cells at various growth stages.

Within the scope of the present invention it has been demonstrated that cells which express the IL-5 receptor and have been transformed with a sensor DNA respond to the addition of IL-5, the natural ligand of the IL-5 receptor, by inducing the expression of the reporter gene. (We tested, on the one hand, murine cells which naturally express the β-subunit and which were additionally transformed with the α-subunit, as well as human cells which naturally express the two units necessary for the functional IL-5 receptor.) The sensor DNA used contains as regulatory element either the 1.3 kb 5'-regulatory region of the human ICAM-1-gene, which contains, inter alia, a TRE-element, or the 0.756 kb 5'-regulatory region of the human c-fos-gene, which contains, inter alia, a TRE, a CRE and an SRE. When these cells, which contain endogenous IL-3 and GM-CSF receptors, were stimulated with IL-3 or GM-CSF, induction of reporter gene expression could again be measured. In control cells which were identical to those used above, apart from the absence of the α-subunit of the IL-5 receptor (which mediates the ligand binding to the receptor) the expression of the reporter gene could also be induced by treating with IL-3 or GM-CSF, but not with IL-5.

The present invention provides a sensitive and versatile method of finding substances which specifically influence one or more signal transmission pathways in the cell, depending on the IL-5 receptor. The substances found by means of the process according to the invention act as guide substances for the development of drugs for treating diseases associated with malfunction of the IL-5 receptor or the signal transmission pathway coupled thereto, and may subsequently be investigated in a secondary screening, e.g. in the case of antagonists in a proliferation assay using cell lines, or with primary cells and only then in animal trials, to investigate their pharmacological properties in more detail. The number of animals required will therefore be reduced considerably by using the process according to the invention. The process according to the invention also has the advantage of being automatable, in that the loading of the cell culture vessels, e.g. 96-well microtitre plates, the filling with the solutions of test substance, the incubation and washing steps and the measurement, e.g. using a luminometer in the case of luciferase as the reporter gene product, may be carried out by robots. The process according to the invention is thus suitable for screening programmes with a high throughput capacity, in which for example about 2000 substances or mixtures of substances can be tested per week.

Using the process according to the invention it is possible to detect allosterically active substances and substances which act non-competitively with regard to the ligand binding site.

The process according to the invention also makes it possible to clone receptors which are pharmacologically or biochemically characterised and are known for the ligands. The starting materials used are cDNA or genomic banks, from which pools are transformed into the corresponding cell line. The expression of the receptor is indicated by expression of the reporter gene after the receptor has been activated by the binding of a ligand.

EXAMPLE 1

Preparation of reporter plasmids with elements which are regulatable by secondary messenger substances (sensor-DNA)

a) Construction of the plasmid pBHluc1.3

Figure 1:
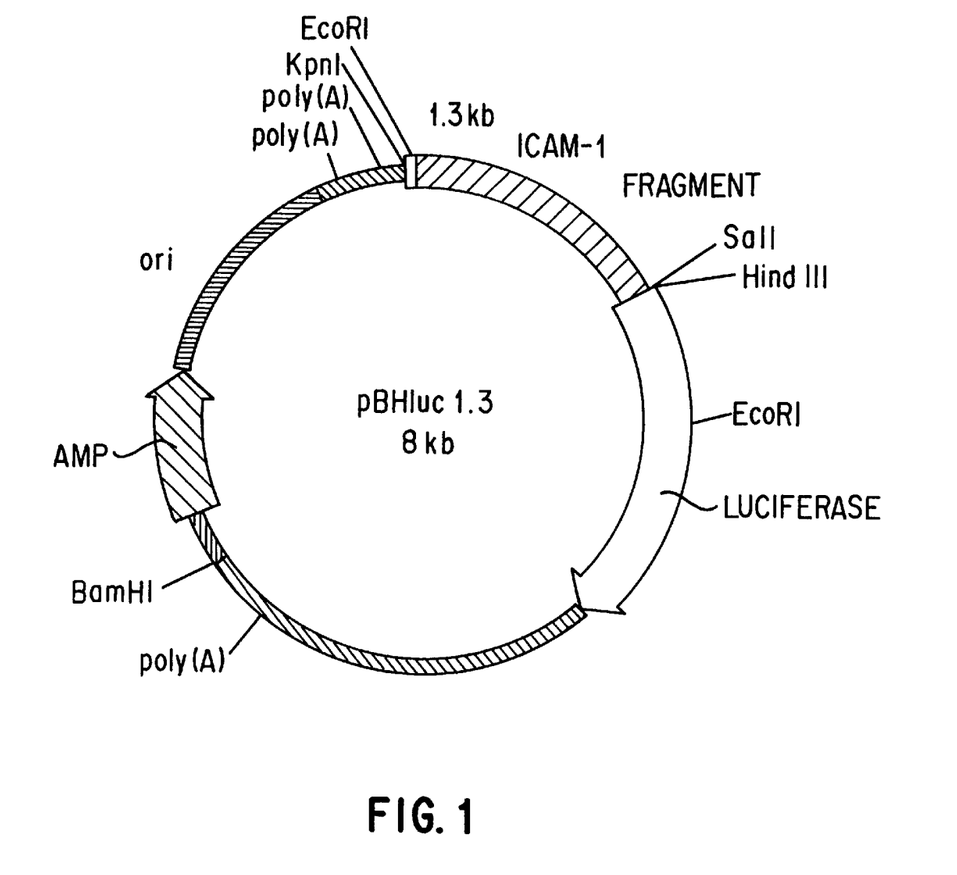
FIG. 1: Sensor DNA plasmid pBHluc1.3, containing the promoter region of the ICAM-1 gene

Cloning and deletion analysis of 1.3 kb of the 5'-flanking region of the human gene for the intercellular adhesion molecule ICAM-1 showed that this fragment i) can be induced by TPA in the lung adenocarcinoma cell line A549 (ATCC CCL 185) and ii) contains a TPA Response Element (TRE) with the DNA sequence TGATTCA (Voraberger et al., 1991). The plasmid pBHluc1.3 (FIG. 1) contains the 1.3 kb long regulating region of the ICAM-1 gene, which precedes the luciferase gene. Its preparation has been described by Voraberger et al., 1991.

b) Construction of the plasmid pBHfosluci

The plasmid pBHfosluci contains the luciferase gene under the control of the promoter of the human c-fos gene, which contains various regulating elements, e.g TRE, CRE and an SRE. A fragment which includes the c-fos promoter (position −711 to +45) was isolated from the plasmid pfosCAT (Schonthal et al., 1988), intermediately cloned in the vector pBluescriptSK (Stratagene) and inserted into the construct pBHluc (Voraberger et al., 1991) in front of the luciferase gene.

Figure 2:
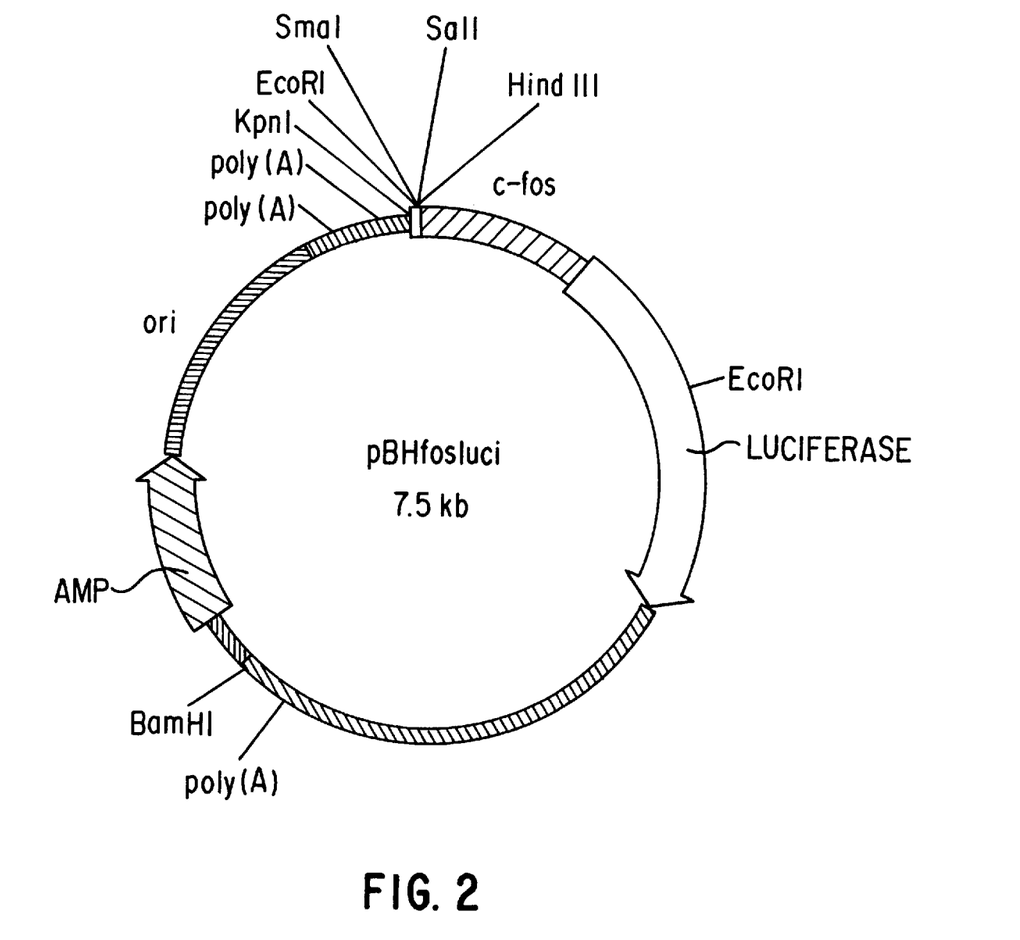
FIG. 2: Sensor DNA plasmid pBHfosluci, containing the promoter region of the c-fos-gene

The plasmid pfosCAT (Schonthal et al., 1988) was cut with XbaI and HindIII. The 756 bp fragment, containing the c-fos promoter, was isolated and ligated with the vector pBluescriptSK, cut with XbaI and HindIII. A plasmid obtained after transformation of E.coli was called pBSfos. The plasmid pBSfos was cut with XbaI, the DNA-ends of the plasmid were made "blunt" by the addition of Klenow enzyme and all 4 dNTPs and finally cut with SalI. The SalI/blunt fragment, containing the c-fos promoter, was isolated. The plasmid pBHluc (Voraberger et al., 1991) was cut with HindIII, the DNA ends were made "blunt" and it was cut with SalI. The vector cut in this way was ligated with the SalI/blunt fragment containing the c-fos promoter. The plasmid obtained after E.coli transformation was called pBHfosluci (FIG. 2).

EXAMPLE 2

Receptor mediated induction of the sensor DNA

In order to show that in cells which express the IL-5 receptor the sensor DNA is induced after stimulation of the receptor with an agonistically acting substance, cells from a murine and from a human cell line were transiently transfected with sensor-DNA (pBHluc1.3 or pBHfosluci):

Murine 1H3-cells were prepared from FDC-P1-cells, a murine, factor dependent cell line established from bone marrow cells (Dexter et al., 1980) by transformation with the α-subunit of the murine IL-5 receptor as follows: a cDNA, coding for the α-subunit of the murine IL-5 receptor (Takaki et al., 1990) was synthesised in a reverse transcriptase PCR reaction (Frohman et al., 1988) using RNA, prepared from the cell line BCL1, clone 5B1b (ATCC TIB 197). The primers used for this purpose were MF71 (SEQ ID NO:1) (5'TCGGCTACCATGGTGCCTGTG3') and MF73 (SEQ ID NO:2) (5'ATGGCAAAATGCCATCAAAACGTG3'); they flank the coding region for the receptor α-subunit (Takaki et al., 1990). (In the list of sequences the synthetic oligodeoxyribonucleotides are given as "cDNS".) The 1272 bp PCR product was subcloned into the SmaI cutting site of the plasmid pUC19 (Pharmacia). The coding sequence was cut out with BamHI and EcoRI and inserted into the expression plasmid pcDNA1 (Invitrogen), cut with the same enzymes. 25 µg of the linearised plasmid were transfected into $4 \times 10^7$ FDC-P1-cells by electroporation (300 V, 96 µF, BioRad Gene Pulser). IL-5 receptor expressing cells were selected in RPMI-1640-medium enriched with murine IL-5. 1H3-cells therefore unlike FCS-P1-cells, which express only the IL-5 receptor β-subunit express a functional IL-5 receptor (α- plus β-subunit). 1H3-cells and FDC-P1-cells have endogenous IL-3 and GM-CSF receptors. The αsubunit is identical in IL-5, IL-3 and GM-CSF receptors.

The human cell line TF-1 was established from bone marrow cells of a patient with erythroleukaemia, as described by Kitamura et al., 1989. The cells express functional receptors for IL-5, IL-3 and GM-CSF, and their proliferation depends on the presence of at least one of the three haematopoetic growth factors (Kitamura et al, 1989, 1991).

One day after transfection of the 1H3- and TF-1-cells with sensor DNA the cells were kept in factor free medium for about 12 hours and then treated with the receptor specific ligand IL-5. As a negative control for the 1H3-cells the same experiment was carried out with murine FDC-P1-cells which do not express the functional IL-5 receptor. In other control experiments, 1H3-, FDC-P1- and FT-1-cells were treated with IL-3 or GM-CSF instead of IL-5.

a) Induction of pBHluc1.3 and pBHfosluci by receptor stimulation in 1H3 cells

Figure 3:
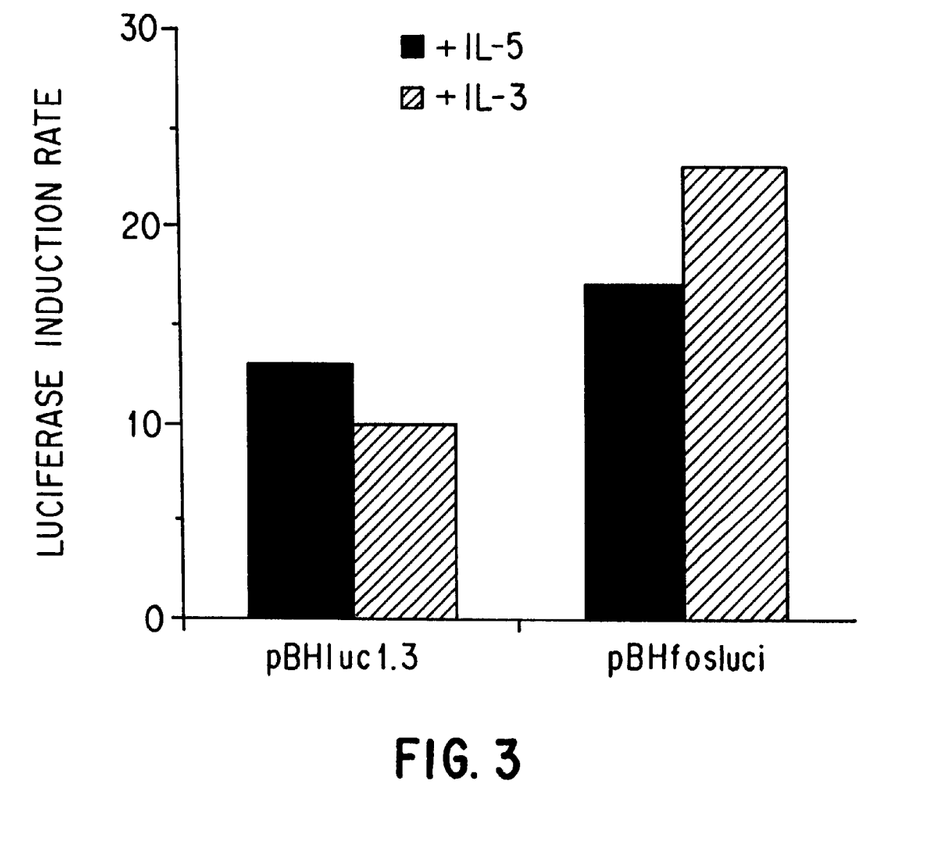
FIG. 3: Induction of pBHluc1.3 and pBHfosluci by receptor stimulation in 1H3-cells

The cell line 1H3, which expresses a functional IL-5 receptor, was cultured in RPMI 1640 medium (Gibco) with 10% heat-inactivated foetal calf serum (FCS) and 1% mouse tonicity supplement (1M NaCl, 0.1M sodium pyruvate, 11.3M monothioglycerol) with the addition of about 500 units/ml of IL-5 (recombinant murine IL-5) at 37° C. in 5% $CO_2$. About $3 \times 10^7$ cells per transfection were centrifuged off for 5 minutes at 1000 rpm and resuspended in 200 µl of medium with all the additives. After the addition of 15 µg of plasmid-DNA per $10^7$ cells the volume was made up to 400 µl using complete medium. The cells were transfected by electroporation in a Biorad Gene Pulser™ with a current pulse of 300 V, 960 µF and then incubated overnight at 37° C. in fresh complete medium containing added IL-5. The next day, the cells were centrifuged for 5 minutes at 1000 rpm and washed twice with IL-5 free complete medium. The cells were resuspended in IL-5 free complete medium and further incubated overnight. For the induction the cells were centrifuged again, resuspended in 60 ml of factor free medium and uniformly divided between three tissue culture flasks. Whilst the cells of one flask were not induced and were kept in factor free medium until the time of the luciferase assay (negative control), the other two were mixed with about 1000 units/ml of IL-5 or IL-3. After 8 hours' incubation at 37° C. the cells were centrifuged off, washed in PBS and taken up in 500 µl of lysing/assay buffer (25 mM tricine, 0.5 mM EDTA, 0.54 mM sodium tripolyphosphate, 6.5 mM DTT, 16.3 mM $MgSO_4.7H_2O$, 0.1% Triton X-100, 1.2 mM ATP, 0.05 mM luciferin; pH 7.8). Of this, 400 µl were measured in the luminometer Lumat 9501 (Berthold) with the addition of 20 µl of luciferin (1 mM). The results of the experiments can be seen in FIG. 3, which shows that both sensor constructs, pBHluc1.3 and pBHfosluci, are more than 10-fold inducible by IL-5. Stimulation of the cells with IL-3 also leads to induction of both sensor constructs via endogenous IL-3 receptors.

b) Induction of pBHluc1.3 by receptor stimulation in FDC-P1 cells

Figure 4:
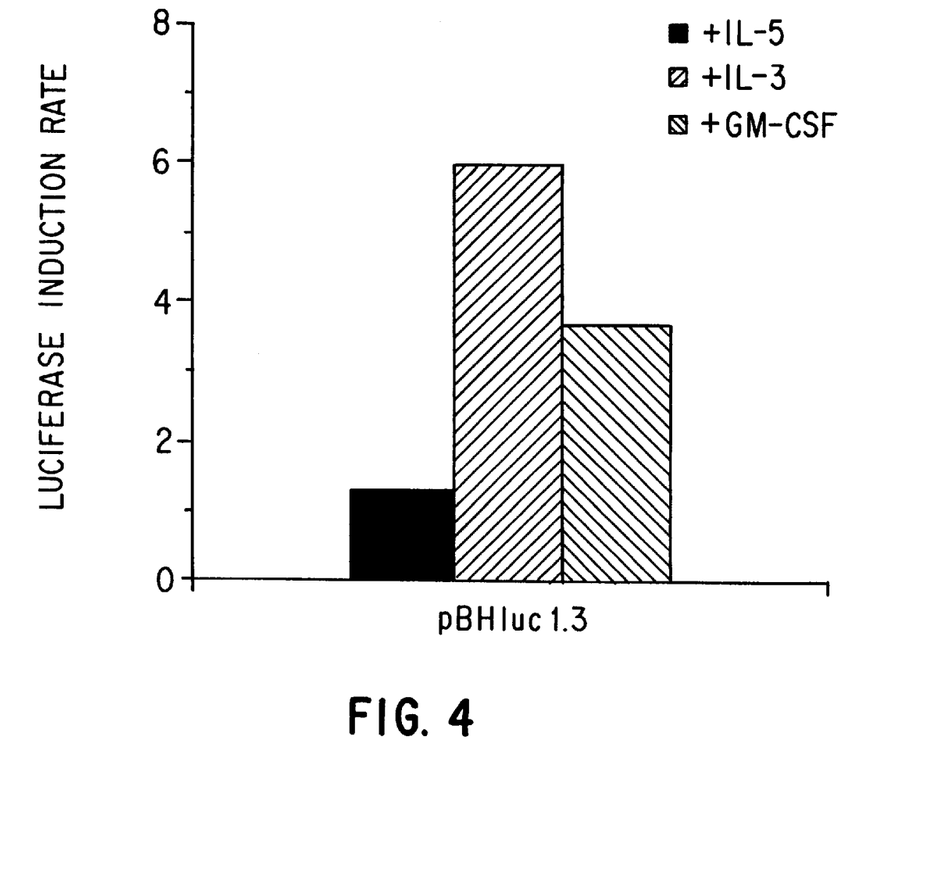
FIG. 4: Induction of pBHluc1.3 by receptor stimulation in murine FDC-P1-cells

The cell line FDC-P1 (Dexter et al., 1980) was cultured in RPMI 1640 medium (Gibco) with the same additives as described for 1H3 cells in a), but with the addition of about 500 units/ml of IL-3 instead of IL-5. About $4 \times 10^7$ cells were transfected by electroporation with 15 µg of pBHluc1.3 DNA per $10^7$ cells, as described in a), incubated and kept in IL-3 free medium. The cells were divided evenly between four tissue culture flasks. The cells of one flask were kept in factor free medium until the luciferase assay was carried out (negative control) whilst the other three were treated with about 1000 units/ml of IL-5, IL-3 or GM-CSF. After 8 hours' incubation, the luciferase assay was carried out as described in a). The results of the experiments can be seen in FIG. 4. The sensor DNA pBHluc1.3 cannot be induced by IL-5 in FDC-P1 cells which express only the β-subunit of the IL-5 receptor whilst the ligand binding α-subunit is absent. By contrast, IL-3 or GM-CSF treatment of the cells leads to induction of the sensor DNA by stimulating the endogenous IL-3 and GM-CSF receptors which are present as in 1H3 cells.

c) Induction of pBHfosluci by receptor stimulation in TF-1-cells

Figure 5:
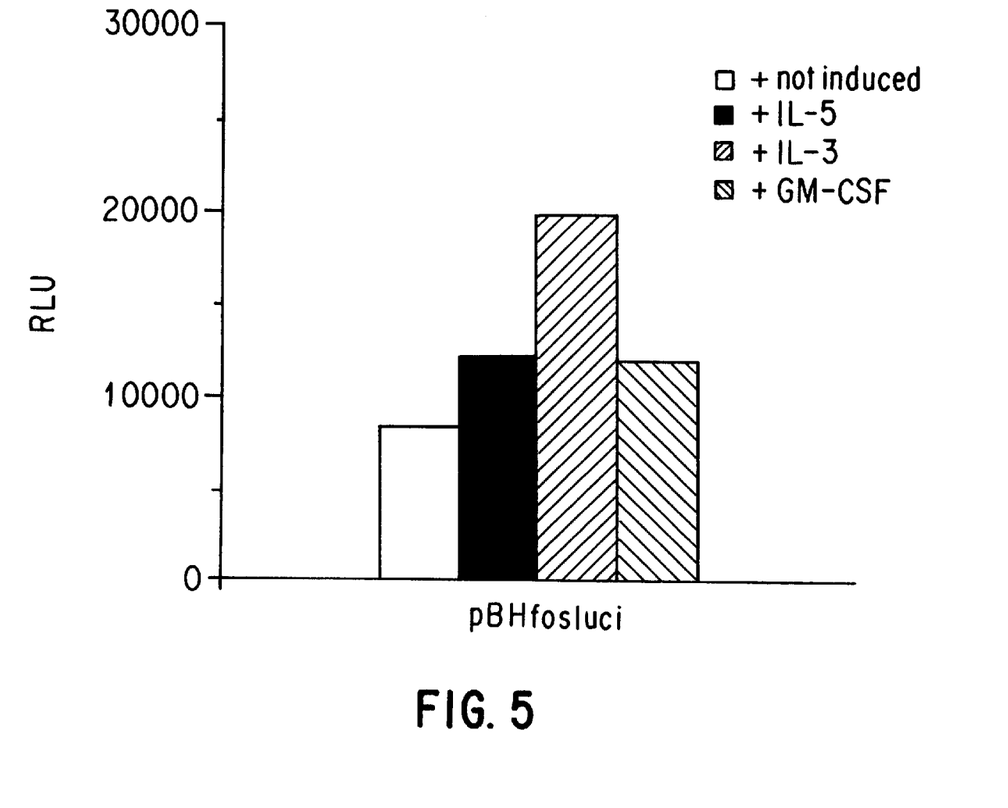
FIG. 5: Induction of pBHluc1.3 by receptor stimulation in human TF-1-cells

The cell line TF-1 was cultured RPMI 1640 medium (Gibco) with 10% heat inactivated foetal calf serum (FCS) with the addition of 1 ng/ml of IL-3 at 37° C. in 5% $CO_2$. About $3 \times 10^7$ cells per transfection were centrifuged off for 5 minutes at 1000 rpm and resuspended in 200 µl of medium with all the additives. After the addition of 15 µg/$10^7$ cells of plasmid-DNA the volume was made up to 400 µl with complete medium. The cells were transfected by electroporation in a Biorad Gene Pulser™ with a current pulse of 280 V, 980 µF and then incubated overnight at 37° C. in fresh complete medium with added IL-3. The next day, the cells were centrifuged for 5 minutes at 1000 rpm and washed twice with IL-3 free complete medium. The cells were resuspended in factor free complete medium and further incubated overnight. For the induction, the cells were centrifuged once again, resuspended in 60 ml of factor free medium and evenly divided between four tissue culture flasks. Whilst the cells in one flask were not induced and were kept in factor free medium until the moment of the luciferase assay (negative control), the other three were combined with about 10 ng/ml of IL-5 or 1 ng/ml of IL-3 or 100 ng/ml of GM-CSF. After 8 hours' incubation at 37° C. the cells were centrifuged off, washed in PBS and taken up in 500 µl of lysing/assay buffer (25 mM tricin, 0.5 mM EDTA, 0.54 mM sodium tripolyphosphate, 6.5 mM DTT, 16.3 mM $MgSO_4.7H_2O$, 0.1% Triton X-100, 1.2 mM ATP, 0.05 mM luciferin; pH 7.8). Of this, 400 µl were measured in the luminometer Lumat 9501 (Berthold) with the addition of 20 µl of luciferin (1 mM). The results of the experiments are shown in FIG. 5 and demonstrate that the sensor construct pBHfosluci can be induced by IL-5 and also by IL-3 and GM-CSF.

d) Induction of the proliferation of TF-1-cells by receptor stimulation

Figure 6:
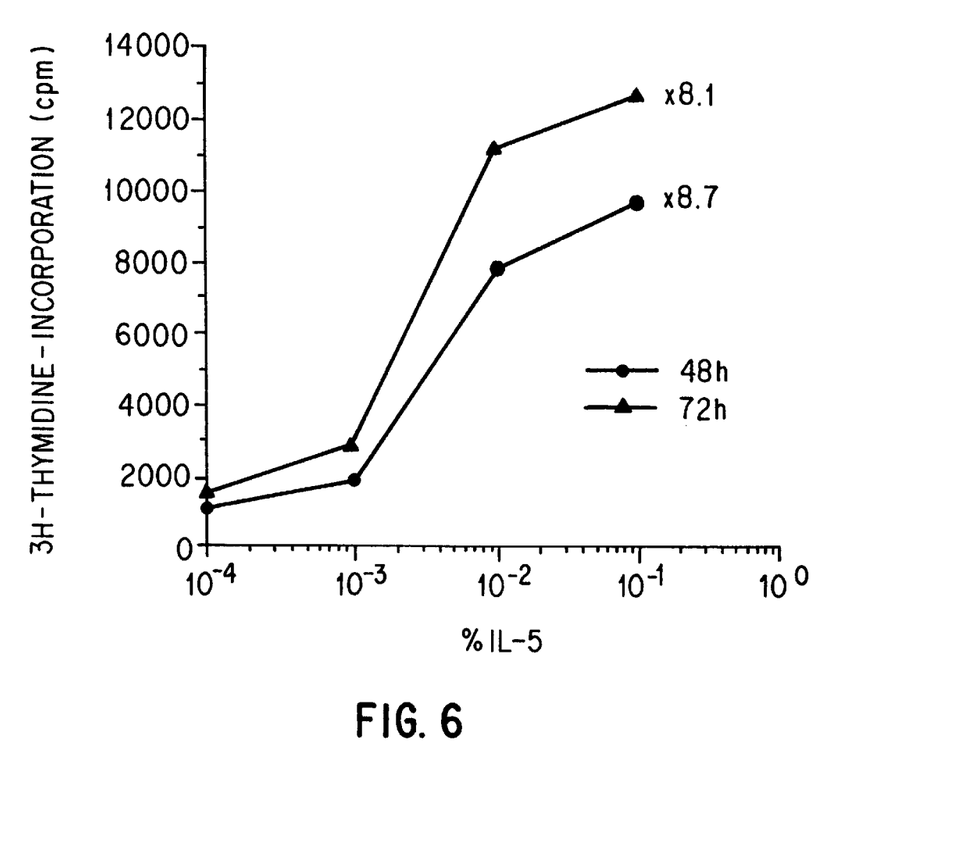
FIG. 6: Induction of the proliferation of TF-1-cells by receptor stimulation

In order to show that TF-1-cells which express the IL-5 receptor proliferate after stimulation of the receptor with an agonistically acting substance, the cells were seeded into 96-well microtitre plates. Two plates were seeded with about $3 \times 10^3$ cells in 100 µl of RPMI 1640 medium containing 2% FCS per well. On each plate, three batches were incubated without IL-5 (negative control) and three batches were mixed with 0.001%, 0.01% and 0.1%, respectively, of recombinant human IL-5. 1 μCi of [6-$^3$H]thymidine (Amersham) was added to each well in the first plate after an incubation time of 48 hours and to the second plate after 72 hours incubation at 37° C. and incubation was then continued for a further 12 hours. The plates were then stored at −20° C. until the incorporation of thymidine was measured using a Packard FilterMate Cell Harvester and TopCount Microplate Scintillation Counter. The results are shown in FIG. 6. At the highest concentration of IL-5 (0.1%) the thymidine incorporation after 48 hours incubation achieved a value of 8.1 times, and after 72 hours, a value of 8.7 times the value for the control cells in medium free from IL-5.

REFERENCES

Akira, S., Isshiki, H., Sugita, T., Tanabe, O., Kinoshita, S., Nishio, Y., Nakajima, T., Hirano, T. and Kishimoto, T., 1990, EMBO J. 9, 1897–1906.

Angel, P., Baumann, I., Stein, B., Delius, H., Rahmsdorf, H. J. and Herrlich, P., 1987a, Mol. Cell. Biol. 7, 2256–2266.

Angel, P., Imagawa, M., Chiu, R., Stein, B., Imbra, R. J., Rahmsdorf, H. J., Jonat, L., Herrlich, P. and Karin, M., 1987b, Cell 49, 729–739.

Billah, M. M., Pai, J.-K., Mullmann, T. J., Egan, R. W. and Siegel, 1989, J. Biol. Chem. 264, 9069–9076.

Brasier, A. R., Tate, J. E. and Habener, J. F., 1989, BioTechniques 7, 1116–1122.

Carroll, M. P., Clark-Lewin, I., Rapp, U. R. and May, W. S., 1990, J. Biol. Chem. 265, 19812–19817.

Deutsch, P. J., Hoeffler, J. P., Jameson, J. L. and Habener, J. F., 1988, Proc.Natl.Acad.Sci. USA 85, 7922–7926.

De Wet, J. R., Wood, K., DeLuca, M., Helinski, D. and Subramani, S., 1987, Mol. Cell. Biol. 7, 725–737.

Devos, R. et al., 1991, EMBO J. 10, 2133–2137.

Dexter, T. M., Garland, J., Scott, D., Scolnick, E. and Metcalf, D., 1980, J. Exp. Med. 152, 1036–1047.

Felgner, P. L., Gadek, T. R., Holm, M., Roman, R., Chan, H. N., Wenz, M., Northrop, J. P., Ringold, G. M., and Danielsen, M., 1987, Proc.Natl.Acad.Sci. USA 84, 7413–7417.

Frohman et al., 1988, Proc.Natl.Acad.Sci. USA 85, 8998–9002.

Gillis, S., 1991, Current Opinion in Immunology 3, 315–319.

Gritz, L. and Davies, J., 1983, Gene 25, 179–188.

Hanazono, Y., Chiba, S., Sasaki, K., Mano, H., Miyajima, A., Arai, K.-i.; Yazaki, Y. and Hirai, H., 1993, EMBO J. 12, 1641–1646.

Hartmann, A., 1991, BioTec 5, 40–45.

Hatakeyama M., Mori, H., Doi, T. and Taniguchi, T., 1989, Cell 59, 837–845.

Hatakeyama M., Kawahara, A., Mori, H., Shibuya, H. and Taniguchi, T., 1992, Proc.Natl.Acad.Sci. USA 89, 2022–2026.

Himmlet, A., et al., 1993, Journal of Receptor Research 13, 79–94.

Hipskind, R. A. and Nordheim, A., 1991, J. Biol. Chemistry 266, 19583–19592.

Houslay, M. D., 1991, Eur. J. Biochem. 195, 9–27.

Isfort, R., Huhn, R. D., Frackelton, A. R., Jr. and Ihle, J. N., 1988, J. Biol. Chem. 263, 19203–19209.

Jantzen et al., 1987, Cell 49, 29–38.

Julius, D., Huang, K. N., Livelli, T. J., Axel, R. and Jessell, T. M., 1990, Proc.Natl.Acad.Sci. USA 87, 928–932.

King, K., Dohlman, H. G., Thorner, J., Caron, M. G. and Lefkowitz, R. J., 1990, Science 250, 121–123.

Kitamura, T., Tange, T., Terasawa, T., Chiba, S., Kuwaki, T., Miyagawa, K., Piao, Y.-F., Miyazono, K., Urabe, A. and Takaku, F., 1989, J. Cell. Physiolog. 140, 323–334.

Kitamura, T., Takaku, F. and Miyajima, A., 1991, International Immunology 3, 571–577.

Koyasu, S., Tojo, A., Miyajima, A., Akiyama, T., Kasuga, M., Urabe, A., Schreurs, J., Arai, K-i., Takaku, F. and Yahara, I., 1987, EMBO J. 6, 3979–3984.

Kricka, L. J., 1988, Analyt. Biochem. 175, 14–21.

Lee, W., Mitchell, P. and Tjian, R., 1987, Cell 49, 741–752.

Landschulz, W. H., Johnson, P. F. and McKnight, S. L., 1988, Science 240, 1759–1764.

Milburn, M. V., Hassell, A. M., Lambert, M. H., Jordan, St.R., Proudfoot, A. E. I., Graber, P. and Wells T. N. C., 1993, Nature 363, 172–176.

Miyajima, A., Kitamura, T., Harada, N., Yokota, T. and Arai, K., 1992, Annu. Rev. Immunol. 10, 295–311.

Montmayeur, J.-P. and Borrelli, E., 1991, Proc.Natl.Acad.Sci. USA 88, 3135–3139.

Montminy, M. R., Gonzalez, G. A. and Yamamoto, K. K., 1990, Trends Neurosci. 13, 185.

Morla, A. O., Schreurs, J., Miyajima, A. and Wang, J. Y. J., 1988, Mol. Cell. Biol. 8, 2214–2218

Mulligan, R. and Berg, P., 1981, Proc.Natl.Acad.Sci. USA 78, 2072–2076.

Murata, Y., Yamaguchi, N., Hitoshi, Y., Tominaga, A. and Takatsu, K., 1990, Biochem. Biophys. Res. Commun. 173, 1102–1108.

Murata, Y., Takaki, S., Migita, M., Kikuchi, Y., Tominaga, A. and Takatsu, K., 1992, J. Exp. Med. 175, 341–351.

Potter, H., Weir, L., and Leder, P., 1984, Proc.Natl.Acad.Sci. USA 81, 7161.

Sassone-Corsi, P., Ransone, L. J. and Verma, I. M., 1990, Oncogene 5, 427–431.

Satoh, T., Nakafuku, M., Miyajima, A. and Kaziro, Y., 1991, Proc.Natl.Acad.Sci. USA 88, 3314–3318.

Satoh, T., Uehara, Y. and Kaziro, Y., 1992, J. Biol. Chem. 267, 2537–2541.

Scheidereit et al., 1986, DNA 5, 383–391.

Schönthal, A. et al., 1988, Cell 54, 325–334.

Southern, P. and Berg, P., 1982, J. Mol. Appl. Gen. 1, 327.

Strähle, U. et al., 1987, Proc.Natl.Acad.Sci. USA 84, 7871–7875.

Takaki, S., Tominaga, A., Hitoshi, Y., Mita, S., Sonoda, E., Yamaguchi, N. and Takatsu, K., 1990, EMBO J. 9, 4367–4374.

Takaki, S., Mita, S., Kitamura, T., Yonehara, S., Yamaguchi, N., Tominaga, A., Miyajima, A. and Takatsu, K., 1991, EMBO J. 10, 2833–2838.

Tavernier, J., Devos, R., Cornelis, S., Tuypens, T., Van der Heyden, J., Fiers, W. and Plaetinck, G., 1991, Cell 66, 1175–1184.

Tominaga, A., Takaki, S., Hitoshi, Y. and Takatsu, K., 1992, BioEssays 14, 527–533.

Treisman, R., 1985, Cell 42, 889–902.

Turner R. and Tjian, R., 1989, Science 243, 1689–1694.

Verma, I. M. and Sassone-Corsi, P., 1987, Cell 51, 513–514.

Voraberger, G., Schäfer, R. and Stratowa, Ch., 1991, J. Immunol. 147, 2777.

Welham, M. J. and Schrader, J. W., 1992, J. Immunol. 149, 2772–2783.

Whetton, A. D., Monk, P. N., Consalvey, S. D., Huang, S. J., Dexter, T. M. and Downes, C. P., 1988, Proc.Natl.Acad. Sci. USA 85, 3284–3288.

Wieland, E. et al., 1985, Ärztl. Lab. 31, 203–214.

Winnacker, E. L., 1985, Gene and Klone, Eine Einführung in die Gentechnologie, VCH Verlagsges. Weinheim, 264.

Yamamoto, K. R., 1985, Annu. Rev. Genet. 19, 209–252.
Cloning Vectors: Chapter VIII, Hsg. Pouwels, Enger-Valk, Brammer, Elsevier, Amsterdam, New York, Oxford, 1985.
Human Pharmacology—Molecular-To-Clinical, Chapter 2: Sites of Action: Receptors, Hsg. Wingard., L. B., Brody, T. M., Larner, J. and Schwartz, A., Mosby Year-Book Inc., St.Louis, 1991.

We claim:

1. A process for screening a test substance for the ability of the test substance to modulate an interleukin-5 receptor-mediated signal transmission pathway in a mammalian cell comprising:

(a) incubating a test mammalian cell with the test substance, wherein said mammalian cell:

(i) is transformed with a recombinant DNA molecule comprising a reporter gene operably linked to a regulatory sequence which responds to a change in intracellular concentration of one or more second messenger substances of said signal transmission pathway, wherein said response is a change in the expression of a reporter gene in said test mammalian cell, said expression being indicated by production of a reporter gene product; and (ii) expresses a functional interleukin-5 receptor;

(b) incubating a control mammalian cell with said test substance, wherein said control mammalian cell:

(i) is transformed with a recombinant DNA molecule comprising a reporter gene operably linked to a regulatory sequence which responds to a change in intracellular concentration of one or more second messenger substances of said signal transmission pathway, wherein said response is a change in the expression of a reporter gene in said test mammalian cell, said expression being indicated by production of a reporter gene product; and (ii) does not express a functional interleukin-5 receptor;

(c) measuring the concentration of said reporter gene product in said test mammalian cell and said control mammalian cell; and (d) comparing the concentration of said reporter gene product in said test mammalian cell to the concentration of said reporter gene product in said control mammalian cell, wherein a higher concentration in said test mammalian cell relative to the concentration in said control mammalian cell indicates that said test substance has activating activity on said signal transmission pathway, and wherein a lower concentration in said test mammalian cell relative to the concentration in said control mammalian cell indicates that said test substance has inhibitory activity on said signal transmission pathway.

2. The process of claim 1, wherein said modulation of said signal transmission pathway is to antagonize said signal transmission pathway, and wherein said process further comprises treating said test and control mammalian cells with interleukin-5 to determine if the test substance has antagonistic activity on said interleukin-5 receptor-mediated signal transmission pathway.

3. The process of claim 1, wherein said test mammalian cell constitutively expresses the β subunit, but not the α subunit, of the native interleukin-5 receptor, and wherein said test mammalian cell is transformed with a recombinant DNA molecule comprising a nucleotide sequence encoding the α subunit of the interleukin-5 receptor.

4. The process of claim 1, wherein said test mammalian cell is transformed with one or more DNA molecules comprising a nucleotide sequence encoding the α subunit of the interleukin-5 receptor, and with one or more DNA molecules comprising a nucleotide sequence encoding the β subunit of the interleukin-5 receptor.

5. The process of claim 4, wherein said nucleotide sequences encoding the α and β subunits of the interleukin-5 receptor are contained on separate DNA molecules.

6. The process of claim 4, wherein said nucleotide sequences encoding the α and β subunits of the interleukin-5 receptor are contained on the same DNA molecule.

7. The process of claim 1, wherein said functional interleukin-5 receptor expressed by said test mammalian cell is a human interleukin-5 receptor.

8. The process of claim 1, wherein said functional interleukin-5 receptor expressed by said test mammalian cell is a murine interleukin-5 receptor.

9. The process of claim 1, wherein said functional interleukin-5 receptor comprises an a subunit and a β subunit, and wherein said ax subunit originates from a different animal species than said β subunit.

10. The process of claim 9, wherein said α subunit is of human origin.

11. The process of claim 1, wherein said regulatory sequence of step (a) is the promoter of the c-fos gene.

12. The process of claim 1, wherein the regulatory sequence of step (a) or step (b) is the promoter of the ICAM-1 gene.

13. The process of claim 1, wherein said reporter gene of step (a) or step (b) is a luciferase gene.

14. A process for screening a test substance for antagonistic activity on an interleukin-5 receptor-mediated signal transmission pathway, comprising (a) identifying a test substance having inhibitory activity on an interleukin-5 receptor-mediated signal transmission pathway according to the screening process of claim 1, wherein said modulation of said signal transduction pathway is to inhibit said signal transduction pathway;

(b) obtaining a first and a second populations of cells, wherein said first and second populations of cells express functional interleukin-5 receptors and are dependent upon the presence of interleukin-5 for growth in veiro;

(c) culturing said first population of cells in the presence of interleukin-5;

(d) culturing said second population of cells in the presence of interleukin-5 and said test substance;

(e) measuring the proliferation of said first and second populations of cells; and (f) comparing the proliferation of said second population of cells to the proliferation of said first population of cells, wherein a decreased proliferation of said second population relative to the proliferation of said first population indicates that said test substance has antagonistic activity on said interleukin-5 receptor-mediated signal transmission pathway.

15. The process of claim 14, wherein said control mammalian cell expresses a functional interleukin-3 receptor.

16. A transformed mammalian cell that expresses a functional interleukin-5 receptor, said cell comprising:

(a) a first recombinant DNA molecule comprising a reporter gene operably linked to a regulatory sequence which responds to a change in intracellular concentration of one or more second messenger substances of an interleukin-5 receptor-mediated signal transmission pathway, wherein said response is a change in the expression of said reporter gene in said test mammalian cell, said expression being indicated by production of a reporter gene product; and (b) a second recombinant DNA molecule comprising a nucleotide sequence encoding the α subunit of a mammalian interleukin-5 receptor.

17. The transformed mammalian cell of claim 16, wherein said second recombinant DNA molecule also encodes the β subunit of the interleukin-5 receptor.

18. The transformed mammalian cell of claim 16, wherein said cell is a human cell.

19. The transformed mammalian cell of claim 16, wherein said cell is a murine cell.

20. The transformed mammalian cell of claim 16, wherein said mammalian cell constitutively expresses the β subunit of the native interieukin-5 receptor.

21. The transformed mammalian cell of claim 20, wherein said α subunit originates from a different mammalian species than said β subunit.

22. The transformed mammalian cell of claim 16, wherein said α subunit is a human α subunit.

23. The transformed mammalian cell of claim 16, wherein said α subunit is a murine α subunit.

24. The transformed mammalian cell of claim 16, wherein said regulatory sequence is the promoter of the c-fos gene.

25. The transformed mammalian cell of claim 16, wherein said regulatory sequence is the promotes of the ICAM-1 gene.

26. The transformed mammalian cell of claim 16, wherein said reporter gene is a luciferase gene.

* * * * *

UNITED STATES PATENT AND TRADEMARK OFFICE
CERTIFICATE OF CORRECTION

PATENT NO. : 5,922,549

DATED : July 13, 1999

INVENTORS : Czernilofsky *et al.*

It is certified that an error appears in the above-identified patent and that said Letters Patent is hereby corrected as shown below.

Column 21, line 36 (claim 9, line 2), after "an", please delete "a" and insert therefor --α--.

Column 21, line 37 (claim 9, line 3), please delete "ax" and insert therefor --α--.

Column 22, line 3 (claim 14, line 14), please delete "in veiro" and insert therefor --in vitro--

Column 22, line 42 (claim 20, line 3), please delete "interieukin-5" and insert therefor --interleukin-5--.

Column 22, line 53 (claim 25, line 2), please delete "promotes" and insert therefor --promoter--.

Signed and Sealed this

Fourth Day of January, 2000

*Attest:*

*Attesting Officer*

*Acting Commissioner of Patents and Trademarks*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (ii) MOLECULE TYPE: cDNA    (iv) ANTI-SENSE: NO    (ix) FEATURE:
      (A) NAME/KEY: 5'UTR
      (B) LOCATION: 1..21

(xi) SEQUENCE DESCRIPTION: SEQ ID NO:1:

TCGGCTACCA TGGTGCCTGT G                    21

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear    (ii) MOLECULE TYPE: cDNA    (iv) ANTI-SENSE: NO    (ix) FEATURE:
      (A) NAME/KEY: 5'UTR
      (B) LOCATION: 1..24

(xi) SEQUENCE DESCRIPTION: SEQ ID NO:2:

ATGGCAAAAT GCCATCAAAA CGTG                 24